US010058709B2

(12) United States Patent
Tilton, Jr.

(10) Patent No.: US 10,058,709 B2
(45) Date of Patent: Aug. 28, 2018

(54) INTEGRATED WIRELESS COMMUNICATIONS FOR AUTOMATED EXTERNAL DEFIBRILLATOR (AED)

(71) Applicant: Verizon Patent and Licensing Inc., Basking Ridge, NJ (US)

(72) Inventor: Teddy D. Tilton, Jr., Warren, NJ (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 32 days.

(21) Appl. No.: 14/815,173

(22) Filed: Jul. 31, 2015

(65) Prior Publication Data
US 2017/0028211 A1 Feb. 2, 2017

(51) Int. Cl.
*A61N 1/39* (2006.01)
*G06F 19/00* (2018.01)

(52) U.S. Cl.
CPC ......... *A61N 1/3925* (2013.01); *A61N 1/3993* (2013.01); *G06F 19/3418* (2013.01)

(58) Field of Classification Search
None
See application file for complete search history.

(56) References Cited

U.S. PATENT DOCUMENTS

| | | | | |
|---|---|---|---|---|
| 4,102,332 A | * | 7/1978 | Gessman | A61B 5/0002 600/513 |
| 8,086,320 B2 | * | 12/2011 | Saketkhou | A61N 1/39 607/30 |
| 9,248,306 B2 | * | 2/2016 | Joo | A61N 1/3987 |
| 2002/0087194 A1 | * | 7/2002 | Russell | A61N 1/39 607/5 |
| 2003/0025602 A1 | * | 2/2003 | Medema | H04W 64/00 340/568.1 |
| 2004/0039420 A1 | * | 2/2004 | Jayne | A61B 5/1107 607/5 |
| 2004/0049233 A1 | * | 3/2004 | Edwards | A61N 1/3931 607/5 |
| 2006/0173499 A1 | * | 8/2006 | Hampton | A61N 1/3925 607/5 |
| 2007/0032830 A1 | * | 2/2007 | Bowers | A61N 1/39 607/5 |
| 2007/0162075 A1 | * | 7/2007 | O'Hara | A61N 1/39 607/5 |
| 2007/0299473 A1 | * | 12/2007 | Matos | A61N 1/0476 607/5 |

(Continued)

*Primary Examiner* — Kennedy Schaetzle (57) ABSTRACT

An automated external defibrillation (AED) device includes a wireless interface to exchange data with one or more other devices. The AED device collects patient data associated with a patient and identifies, based on the patient data, a heart condition associated with the patient. The AED device directs a user to apply defibrillation to the patient to address the heart condition; and forwards via the wireless interface, a notification to a dispatch device. The notification may identify, for example, a location associated with the AED device. The dispatch device may direct emergency medical assistance to the location. The AED device may collect data, used to diagnose the heart condition, from a patient device and via the wireless interface. The AED device may further forward, to a user device and via the wireless interface, instructions guiding the user to use the AED device.

20 Claims, 8 Drawing Sheets

(56) References Cited

U.S. PATENT DOCUMENTS

| | | | |
|---|---|---|---|
| 2008/0097533 A1* | 4/2008 | Halsne | A61N 1/39 607/5 |
| 2010/0017471 A1* | 1/2010 | Brown | A61B 5/0006 709/204 |
| 2011/0060378 A1* | 3/2011 | Tuysserkani | A61B 5/0022 607/5 |
| 2011/0172550 A1* | 7/2011 | Martin | A61B 5/7445 600/523 |
| 2011/0284004 A1* | 11/2011 | Silver | A61B 5/087 128/205.13 |
| 2012/0112903 A1* | 5/2012 | Kaib | A61N 1/3993 340/539.12 |
| 2014/0031884 A1* | 1/2014 | Elghazzawi | A61N 1/39 607/5 |
| 2014/0266718 A1* | 9/2014 | Bongberg | A61N 1/3993 340/540 |
| 2015/0148856 A1* | 5/2015 | Freeman | A61N 1/3987 607/6 |
| 2015/0306409 A1* | 10/2015 | Greiner | A61N 1/3925 607/7 |

* cited by examiner

INTEGRATED WIRELESS COMMUNICATIONS FOR AUTOMATED EXTERNAL DEFIBRILLATOR (AED)

BACKGROUND

An automated external defibrillator (AED) is a device that diagnoses and treats certain types of life-threatening cardiac arrhythmias. The AED may use defibrillation (i.e., applying an electrical current) to stop the arrhythmia and direct the heart to re-establish a normal rhythm. AEDs are designed to be used in public environments and by non-medical operators. AEDs may provide audio prompts and/or visual prompts to guide users. For example, the AED may direct a user to position sensor pads in specific locations on the patient, and the AED may automatically diagnose the heart arrhythmia based on readings collected from the sensor pads. If the AED determines that defibrillation is needed, the AED may direct the user on how to correctly apply the defibrillation to the patient.

DETAILED DESCRIPTION OF PREFERRED EMBODIMENTS

The following detailed description refers to the accompanying drawings. The same reference numbers in different drawings may identify the same or similar elements. Also, the following detailed description does not limit the invention.

Figure 1:
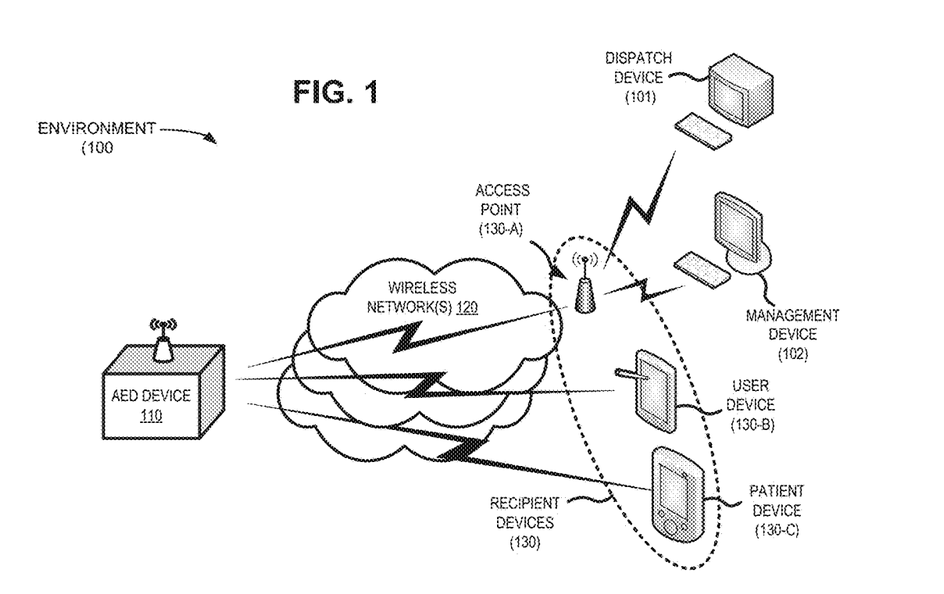
FIG. 1 shows an exemplary environment in which systems and/or methods described herein may be implemented.

FIG. 1 is a diagram of an exemplary environment 100 in which systems and/or methods described herein may be implemented. As shown in FIG. 1, environment 100 may include an automated external defibrillator (AED) device 110 that forwards messages via one or more wireless networks 120 to one or more recipient devices 130 (shown in FIG. 1 as access point 130-A, user device 130-B, and patient device 130-C). As further shown in FIG. 1, environment 100 may further include a dispatch device 101 and/or management device 102 that receive signals from AED device 110 via access point 130-A.

AED device 110 may detect certain types of cardiac arrhythmias and may selectively apply defibrillation (e.g., a controlled electrical current to reset the heart rhythm) when one of the cardiac arrhythmias is detected. For example, if the AED detects ventricular tachycardia (V-Tach) during which the heart beats too fast to effectively pump blood, AED device 110 may apply defibrillation to cause the heart to beat at a slower rate. In another example, if the AED detects ventricular fibrillation (V-Fib) during which portions of the heart are active but operating out of rhythm so that blood is not being circulated, AED device 110 may apply defibrillation to coordinate the portions of the heart. Defibrillation may be ineffective for other heart conditions, such as asystole during which the heart stops beating. If AED device 110 detects a heart condition that is not helped by defibrillation, AED device 110 does not apply defibrillation and may, instead, direct a user to perform other treatments such cardiopulmonary resuscitation (CPR).

AED device 110 may further include a user interface to provide instructions to a user. For example, AED device 110 may include a speaker to provide audio data and/or a display to present visual data. AED device 110 may direct the user on how to properly position sensor pads on a patient to detect a heart condition, and may further direct the user on how to provide defibrillation when AED device 110 detects certain types of heart conditions.

AED device 110 may still further include a wireless interface that enables AED device 110 to communicate with one or more recipient devices 130 via wireless network 120. For example, AED device 110 may include mobile phone circuitry or a mobile phone module to connect to wireless network 120. Additionally or alternatively, AED device 110 may include an interface (e.g., a port to receive a connection or a short-distance wireless interface (e.g., a Bluetooth® interface to connect) user device 130-B/patient device 130-C to communicate with wireless network 120.

Wireless network 120 may include a communications network, a data network, or a combination of networks that connect AED device 110 and one or more recipient devices 130. For example, wireless network 120 may include or be included in a radio network capable of supporting wireless communications to/from one or more devices in environment 100, and the radio network may include, for example, a fourth generation (4G) long-term evolution (LTE) network (4G LTE), another 3rd Generation Partnership Project (3GPP) 3G/4G network, Global System for Mobile Communications (GSM), wideband code division multiple access (WCDMA), Ultra Mobile Broadband (UMB), Universal Mobile Telecommunications System (UMTS), Code Division Multiple Access 1000 (CDMA2000), High-Speed Packet Access (HSPA), Worldwide Interoperability for Microwave Access (WiMax), enhanced high-rate packet data (eHRPD), or a network implemented in accordance with other wireless network standards, including future wireless network standards.

In another example, wireless network 120 may connect AED device 110 and recipient device 130 located at a common location. For example, wireless network 120 may be a wireless local area network (WLAN) based on the International Electrical and Electronics Engineers 802.11 protocol, or other short-range network via which AED device 110 and recipient device 130 may communicate. For example, AED device 110 and recipient device 130 may communicate via Bluetooth®, Wi-Fi®, and/or another short-range wireless network protocol. In another example, AED device 110 and recipient device 130 may communicate via a near field communication ("NFC") or an infrared-based communications such as Infrared Data Association (IrDA) protocols. In yet another example, AED device 110 and a recipient device 130 may communicate via a wired connection, such as a universal serial bus (USB) cable or other wired connection.

In one implementation, access point 130-A may enable AED device 110 to communicate with a remote dispatch device 101 (e.g., a device used to request emergency services) and/or a remote management device 102 (e.g., a device that manages one or more AED devices 110 associated with a location and/or an entity). Access point 130-A may correspond, for example, to a base station, a wireless router, or other a device that handles wireless transmissions to and from AED device 110 via wireless network 120. Access point 130-A may include antennas and related transceiver circuitry for connecting to AED device 110 over wireless network 120. For example, access point 130-A may include a wireless station, such as an eNodeB in a Long Term Evolution (LTE) system, a Node B in a UMTS, a base transceiver station (BTS) in a Global System for Mobile Communications (GSM) system, etc. Additionally, or alternatively, access point 130-A may be associated with a wireless network that is not associated with an LTE network (e.g., a wireless hot spot, a wireless access point, a 3G/2G base station, etc.).

Additionally or alternatively, access point 130-A may include a device for amplifying a signal, coding/decoding a signal and/or forwarding a signal (e.g., a repeater or a relay). Additionally, or alternatively, access point 130-A may include a device for attaching and/or inserting an additional signal or information to a signal before forwarding, amplifying, and/or decoding it. In this regard, access point 130-A is intended to be broadly interpreted to include any type of node that may perform one or more operations in accordance with a wireless environment.

For example, when AED device 110 is activated, AED device 110 may forward a notification, via access point 130-A, to dispatch device 101 to request emergency assistance. AED device 110 may include, in the notification, information associated with the patient, such as collected sensor readings, data collected by AED device 110 from user device 130-B and/or patient device 130-C, data identifying a heart condition detected by AED device 110 based on the sensor readings, and/or any treatment (e.g., defibrillation) applied by AED device 110. Likewise, the notification may also include information associated with AED device 110, such as an associated geographic location, a device type, model, etc.

In one implementation, AED device 110 may enable voice communications (e.g., a telephone call) between the user and an operator of dispatch device 101. For example, AED device 110 may include a button that automatically dials "911" or another emergency telephone number associated with receiving help. In another example, AED device 110 may include an audio sensor (e.g., a microphone) that detects voice commands by the user, and AED device 110 may dial an emergency telephone number when certain types of voice commands (e.g., "Dial 911") are detected. In another implementation, AED device 110 may communicate, via access point 130-A, with dispatch device 101 using machine-to-machine (M2M) communications. M2M communications automate a variety of data gathering operations and/or provide automatic data communications in support of a variety of other automated applications so that emergency response services may be automatically dispatched when AED device 110 is used (e.g., when a heart condition is detected). In this way, the emergency response services may be dispatched to a geographic location associated with AED device 110 even when a user does not have a communications device and/or the user is occupied attending to a patient. Furthermore, the emergency response services may be dispatched without requiring the user to stop attending to the patient to request assistance.

Additionally or alternatively, AED device 110 may forward a status indication, via access point 130-A, to management device 102. AED device 110 may include, in the status indication, an indication of the use (e.g., use of the sensor pads) and/or treatment (e.g., defibrillation) applied by AED device 110. The status information may also include other data identifying a status of AED device 110 and/or indicate whether AED device 110 is ready to be used (e.g., fully charged, in need of maintenance, includes recent programming, etc.). AED device 110 may also forward the status indication when AED device 110 is not used. For example, AED device 110 may forward the status information to management device 102 periodically (e.g., weekly) or based on receiving a request from management device 102.

In one implementation, AED device 110 may communicate, via access point 130-A, with management device 102 using M2M communications. For example, M2M communications may be used to forward the status message to management device 102. Thus, automated M2M communications, may help eliminate a need for a maintenance official to personally visit a premises and manually inspect AED device 110 to determine whether AED device 110 is operational or needs servicing (e.g., new sensor pads after a use of AED device 110).

In another example, AED device 110 may receive data via access point 130-A. For example, AED device 110 may receive contact information from dispatch device 101 via access point 130-A. The contact information may identify a particular emergency service responder (e.g., an emergency responder geographically proximate to AED device 110) that AED device 110 should notify when AED device 110 is activated. AED device 110 may also receive location information (e.g., global positioning system (GPS) data) from access point 130-A and may forward the location information to dispatch device 101.

In another example, AED device 110 may receive a programming update from management device 102. For instance, management device 102 may update instruction prompts provided by AED device 110 to users. The updated instructions may enable AED device 110 to provide improved prompts (e.g., to correct an error in a prior prompt provided by AED device 110 or to provide enhanced prompts, such as prompts with visual instructions to be output to a display include with the AED device 110, such as an LCD screen). Additionally or alternatively, management device 102 may update treatment used by AED device 110, such as to change the parameters of defibrillation (e.g., voltage, current, frequency, etc.) applied by AED device 110 to a patient in response to detecting certain types of heart conditions.

AED device 110 may also communicate via wireless networks 120 with user device 130-B (e.g., associated with a user) and/or patient device 130-C (e.g., associated with a patient being diagnosed and/or treated by AED device 110).

Each of user device 130-B and patient device 130-C may include a computation or communication device that communicates with AED device 110 via wireless network 120. For example, each of user device 130-B and patient device 130-C may include a cellular telephone; mobile phone circuitry or a mobile phone module to connect to wireless network 120; a personal communications system (PCS) terminal (e.g., that may combine a cellular telephone with data processing and data communications capabilities); a personal digital assistant (PDA) (e.g., that can include a radiotelephone, a pager, Internet/intranet access, etc.); a smart phone; a laptop computer; a tablet computer; a camera; a personal gaming system, a wearable computer, or another type of mobile computation and communication device. Each of user device 130-B and patient device 130-C may also, or alternatively, include one or more components such as global positioning system (GPS) components (not shown) that enable a location, associated with user device 130-B and/or patient device 130-C to be identified. In another example, patient device 130-C may correspond, for example, to a fitness device, smart watch, etc., that detects biometric data associated with the patient.

AED device 110 may communicate with user device 130-B to obtain information associated about the user, such as the user's name, telephone number, address, etc. This information may be provided to emergency response personnel (e.g., responders dispatched by dispatch device 101) to enable the emergency response personnel to communicate with the user, if needed. A communication (e.g., telephone call) may be automatically established to user device 130-B in certain situations, such as when AED device 110 applies defibrillation or when AED device 110 detects a heart conditions that cannot be treated by defibrillation. For example, the communication may allow emergency response personnel to direct the user on how to be treat the patient until medical personnel arrives.

In one implementation, AED device 110 may communicate with user device 130-B to identify a language used by the user, such as language selected by the user for user device 130-B to present audio/text data. AED device 110 may use this information to provide prompts/instructions to the user in the user's preferred language.

In another example, other data may be sensed by and collected from user device 130-B, and the information may be forwarded to dispatch device 101. For example, user device 130-B may identify an associated geographic location associated with the use of AED device 110. This may be useful since AED device 110 is portable may be moved from a storage location and used in a different location associated with the patient (e.g., a different floor or room in a building). In this way, emergency response personnel may be able to locate the user with a minimum delay. The user device 130-B may also collect image data, temperature data, movement data, audio data, etc., that may be provided, for example, to emergency response personnel. For example, user device 130-B may collect and forward information regarding the patient, such as the patient's body temperature, position, movements, audio data indicating the patient's heart condition, etc. In another example, user device 130-B may capture image data identifying a positioning of sensors on a patient, and emergency response personnel may indicate to the user whether the sensor positioning is accurate to allow AED device 110 to operate. Thus, the user may receive, via user device 130-B, real-time feedback regarding the use of AED device 110.

In another implementation, AED device 110 may communicate with user device 130-B to forward instructions. For example, AED device 110 may present audio prompts and may use a display in user device 130 to provide visual data and/or instructions related to the use of AED device 110. In this way, AED device 110 may present visual instructions via user device 130-B even if AED device 110 does not include display capabilities.

Additionally or alternatively, AED device 110 may communicate with patient device 130-C to obtain contact information associated with the patient, such as the patient's name, telephone number, address, medical history, etc. This information may be provided to emergency response personnel (e.g., responders dispatched by dispatch device 101) to enable the emergency response personnel to contact family members, if desired. For example, patient device 130-C may forward the patient's medical history (e.g., whether the patient has previously had an arrhythmia or other heart condition or is associated with other health conditions, prior medical procedures performed on the patient), data identifying what medications the patient has taken and when those medications were taken, data identifying the patient's doctor(s), care directives (e.g., information identifying known conditions, the patient's allergies, whether the patient has identified specific treatments to be performed, etc.), data identifying contacts/family members associated with the patient, etc.

In another example, other sensor data may be automatically collected from patient device 130-C, and the information may be forwarded to dispatch device 101. For example, patient device 130-C may identify an associated geographic location associated with the patient. In another example, AED device 110 may collect sensor data from patient device 130-C (e.g., accelerometer data). AED device 110 may compare the collected sensor data to historical data collected by patient device 130-C, and may diagnose certain heart conditions based on the comparison. For example, AED device 110 may collect, from patient device 130-C biometric data, identifying an activity (e.g., movement), heartbeat, body temperature, recent activity (i.e., a pedometer algorithm or exertion algorithm that may indicate the level of exertion leading up to a heart attack, etc. of the patient during a time period before AED device 110 is activated. AED device 110 may diagnose the patient at least partially based on comparing the patient data to data associated with known heart conditions. AED device 110 may automatically contact emergency response personnel when certain patient data is detected (e.g., when the heart rate is less than a low threshold value or greater than a high threshold value. In another implementation, AED device 110 may automatically contact dispatch device 101 when certain life-threatening heart conditions are diagnosed. AED device 110 may further forward to dispatch device 101 the sensor readings from patient device 130-C. Additionally or alternatively, AED device 110 may forward the patient data to emergency response personnel.

Environment 100 may include fewer components, additional components, different components, and/or differently arranged components than those illustrated in FIG. 1. Additionally or alternatively, one or more operations described as being performed by a particular component of environment 100 may be performed by one or more other components, in addition to or instead of the particular component of environment 100.

Figure 2:
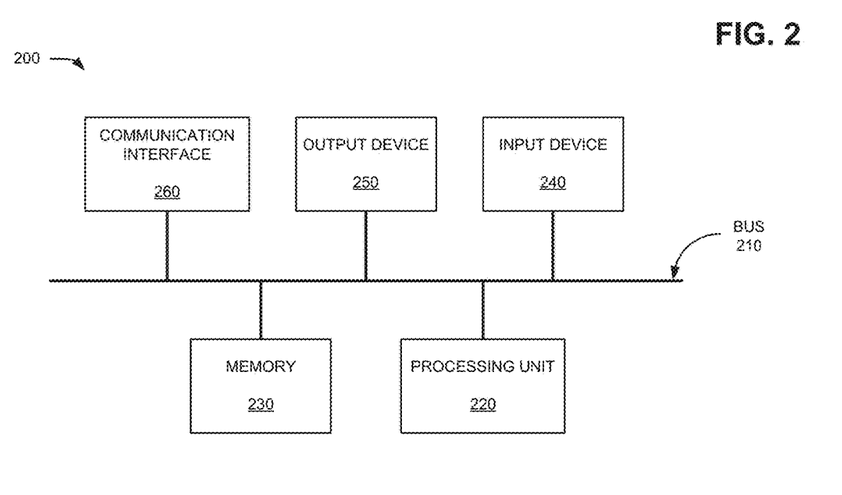
FIG. 2 shows a diagram of exemplary components that may be included in a device included in the environment shown in FIG. 1.

FIG. 2 is a diagram illustrating exemplary components of a device 200. Each of dispatch device 101, maintenance device 102, AED device 110, a component of wireless network 120, access point 130-A, user device 130-B, and/or patient device 130-C may include one or more devices 200. As shown in FIG. 2, device 200 may include a bus 210, a processing unit 220, a memory 230, an input device 240, and output device 250, and a communication interface 260.

Bus 210 may include a path that permits communication among the components of device 200. Processor 220 may include a processor, a microprocessor, or processing logic that may interpret and execute instructions. Memory 230 may include any type of dynamic storage device that may store information and instructions, for execution by processor 220, and/or any type of non-volatile storage device that may store information for use by processor 220. Input device 240 may include a mechanism that permits a user to input information to device 200, such as a keyboard, a keypad, a button, a switch, etc. Output component 250 may include a mechanism that outputs information to the user, such as a display (e.g., a liquid crystal display (LCD)), a speaker, one or more light emitting diodes (LEDs), etc.

Communication interface 260 may include a transceiver that enables device 200 to communicate with other devices and/or systems via wireless communications, wired communications, or a combination of wireless and wired communications. For example, communication interface 260 may include mechanisms for communicating with another device or system via a network. Communication interface 260 may include an antenna assembly for transmission and/or reception of radio frequency (RF) signals. For example, communication interface 260 may include one or more antennas to transmit and/or receive RF signals over the air. Communication interface 260 may, for example, receive RF signals and transmit them over the air. In one implementation, for example, communication interface 260 may communicate with a network and/or devices connected to a network. Alternatively or additionally, communication interface 260 may be a logical component that includes input and output ports, input and output systems, and/or other input and output components that facilitate the transmission of data to other devices.

Device 200 may perform certain operations in response to processing unit 220 executing software instructions contained in a computer-readable medium, such as memory 230. A computer-readable medium may be defined as a non-transitory memory device. A memory device may include space within a single physical memory device or spread across multiple physical memory devices. The software instructions may be read into memory 230 from another computer-readable medium or from another device. The software instructions contained in memory 230 may cause processor 220 to perform processes described herein. Alternatively, hardwired circuitry may be used in place of or in combination with software instructions to implement processes described herein. Thus, implementations described herein are not limited to any specific combination of hardware circuitry and software.

Device 200 may include fewer components, additional components, different components, and/or differently arranged components than those illustrated in FIG. 2. As an example, in some implementations, a display may not be included in device 200. In these situations, device 200 may be a "headless" device that does not include input device 240. Additionally, or alternatively, one or more operations described as being performed by a particular component of device 200 may be performed by one or more other components, in addition to or instead of the particular component of device 200.

Figure 3:
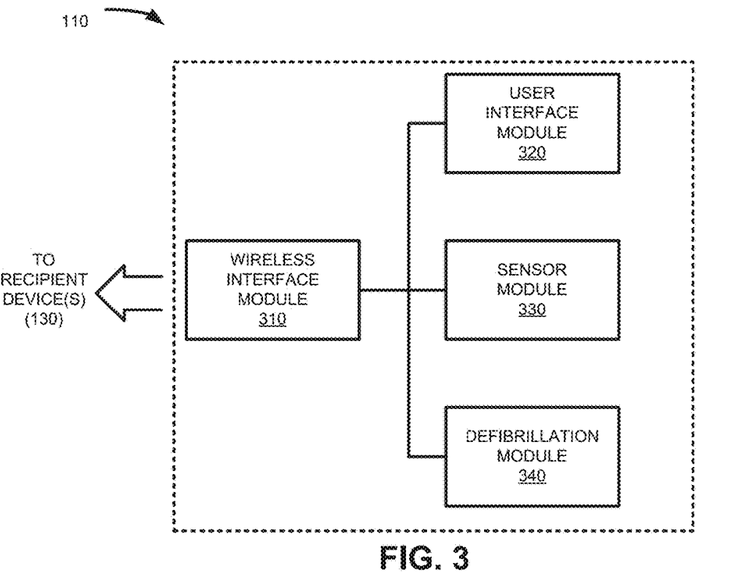
FIG. 3 shows a diagram of exemplary components that may be included in an automated external defibrillator (AED) device included in the environment shown in FIG. 1 according to one implementation.

FIG. 3 is a diagram of exemplary components of AED device 110 according to an implementation described herein. As shown in FIG. 3, AED device 110 may include a wireless interface module 310 to exchange data with one or more recipient devices 130, a user interface module 320 to guide the user to use AED device 110, a sensor module 330 that may collect data regarding the status of the patient's heart or other health attributes, and a defibrillation module 340 that may selectively provide an electrical current based on patient readings by sensor module 330.

Wireless interface module 310 may include a transceiver that enables AED device 110 to communicate with one or more recipient devices via wireless communications. For example, wireless interface module 310 may include mechanisms for communicating via one or more wireless networks 120, such as a 4G or other wireless wide area networks and/or a WI-FI®, Bluetooth or other local area network (LAN). Wireless interface module 310 may include an antenna assembly for transmission and/or reception of radio frequency (RF) signals. For example, wireless interface module 310 may include one or more antennas to transmit and/or receive different RF bands over the air. For example, the antennas may include a directional and/or omnidirectional antenna for receiving wireless signals included in M2M bands and/or voice/data bands. Wireless interface module 310 may further include a logical component that encodes/decodes data for transmission via the RF signals. As previously described, wireless interface module 310 may automatically notify dispatch device 101 to request emergency assistance. For example, wireless interface module 310 may send a notification when AED device 110 is used and/or when certain heart conditions are detected by sensor module 330. In one implementation, wireless interface module 310 may include a wide area communication portion to communicate with a remote access point 130-A (such as a base station) and a local communication portion to communicate with user device 130-B and/or patient device 130-C.

User interface module 320 may include one or more components to present instructions to a user, such as a speaker for providing audio data and/or a display for presenting graphical data. In another example, user interface module 320 may interact with wireless interface module 310 to forward data to another device (e.g., user device 130-B) that provide audio/visual instructions to the user. User interface module 320 may further include a button or other input mechanism that allows the user to initiate a telephone call to request emergency assistance.

Sensor module 330 may include one or more sensors to detect and diagnose a heart condition in the patient. For example, sensor module 330 may include one or more sensor pads that are applied to the user to detect electrical heart impulses, and sensor module 330 can use the detected electrical heart impulses to identify whether the patient is suffering from a life-threatening heart condition. In one implementation, sensor module 330 may work with wireless interface module 310 to receive sensor data from another device (e.g., patient device 130-C). For example, sensor module 330 may collect data from an accelerometer or other sensor in patient device 130-C, and sensor module 330 may use compare these sensor readings with sensor data associated with heart conditions to diagnose the patient.

Defibrillation module 340 may selectively apply defibrillation to the patient when certain types of heart conditions are detected by sensor module 330. For example, user interface module 320 may direct the user to perform certain actions, such as positioning defibrillation contacts at certain locations on the patient and activating the defibrillation once the contacts are positioned.

AED device 110 may include fewer components, additional components, different components, and/or differently arranged components than those illustrated in FIG. 3. Additionally, or alternatively, one or more operations described as being performed by a particular component of AED device 110 may be performed by one or more other components, in addition to or instead of the particular component of AED device 110.

Figure 4:
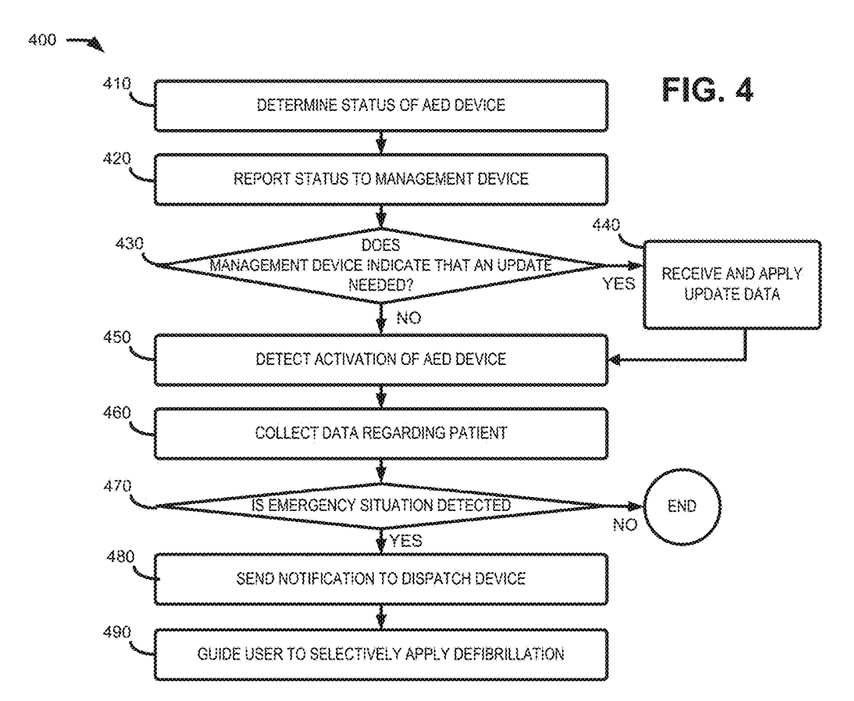
FIG. 4 shows a flow diagram illustrating an exemplary process for exchanging wireless signals by the AED device in the environment shown in FIG. 1 according to one implementation.

FIG. 4 is a flow diagram illustrating an exemplary process 400 for exchanging wireless communications by AED device 110. In one implementation, process 400 may be performed by AED device 110. In other implementations, process 400 may be performed by one or more other devices of environment 100, such as access point 130-A.

As shown in FIG. 4, process 400 may include determining a status of AED device 110 (e.g., prior to the AED device 110 being activated for use with a patient) (block 410) and reporting the status to management device 102 (block 420). For example, AED device 110 may perform a diagnostic health check and forward results of the health check to management device 102 via wireless network 120. For example, AED device 110 may forward an M2M communication identifying its status to management device 102 using wireless interface module 310. Wireless interface module 310 of AED device 110 may receive a response from management device 102, and AED device 110 may determine whether the response indicates that an update is needed by AED device 110 (block 430). If an update is needed (block 430—Yes), AED device 110 may receive update data from management device 102 or another source (block 440). For example, AED device 110 may parse a response received from management device 102 to determine whether it includes update data and/or data (e.g., a uniform resource identifier) that may be used by AED device 110 to obtain the update data.

As shown in FIG. 4, process 400 may further include detecting activation of AED device 110 (block 450) and collecting data regarding the patient when AED device 110 is activated (block 460). For example, AED device 110 may include an activation button, and AED device 110 may detect when the activation button is selected by the user. After activation of AED device 110, user interface module 320 may direct the user to apply sensor pads of sensor module 330 at appropriate portions of the patient's body to detect the patient's heart function. Sensor module 330 may further direct wireless interface module 310 to communicate with user device 130-B and or patient device 130-C to collect sensor data regarding the patient. For example, AED device 110 may cause user device 130-B to present a graphical user interface (GUI) that prompts the user to input information regarding the patient (e.g., describing the appearance of the user, responses of the patient to questions, etc.)

As shown in FIG. 4, process 400 may also include determining, based on the collected patient data, whether an emergency situation (i.e., when the patient's life is threatened) is occurring (block 470). For example, AED device 110 may identify whether the patient has a heart condition that can be treated through defibrillation and/or requires assistance from emergency medical personnel. If AED device 110 determines that the patient data does not indicate an emergency situation (block 470—No), process 400 may end (e.g., user interface module 320 may direct the user to not apply defibrillation to the patient).

If AED device 110 determines that the patient data indicates an emergency situation (block 470—Yes), AED device 110 may forward, via wireless interface module 310, a notification to dispatch device 101, requesting emergency medical assistance (block 480). The notification may include, for example, information regarding the patient collected in block 460. AED device 110 may also guide, via user interface module 320, the user to selectively apply defibrillation to the patient using defibrillation module 340 when AED device 110 determines that the patient's detected heart condition can be treated through defibrillation (block 490).

Figure 5:
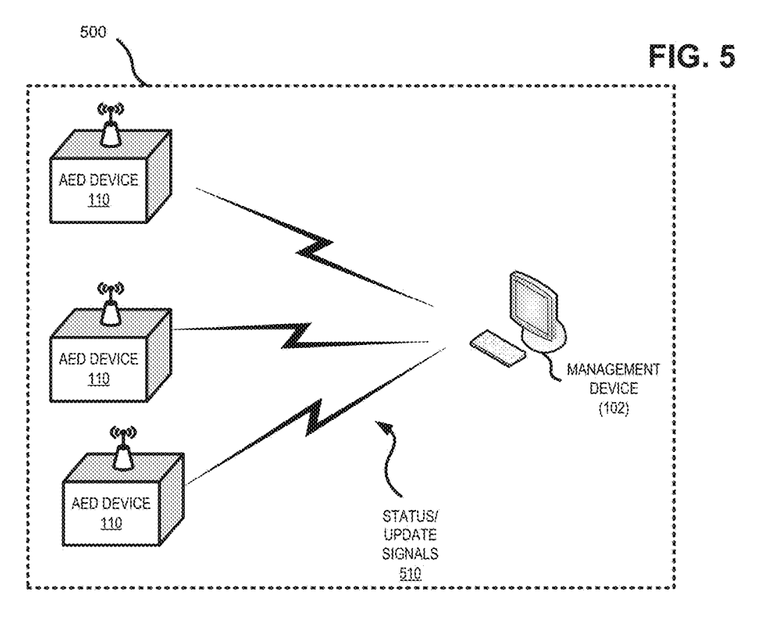
FIGS. 5, 6, and 7A-7B show examples of wireless signals exchanged by the AED device in the environment shown in FIG. 1 according to various implementations.

In one example, shown in FIG. 5, a customer premise 500 (e.g., an office, an apartment building, a campus, etc.) may include multiple AED devices 110. AED devices 110 and management device 102 may exchange status update signals 510 identifying the status of the AED devices 110 and forwarding update information to AED devices 110. In this way, management device 102 may verify that multiple AED devices 110 are operational and may forward update data with minimum manual activity.

Figure 6:
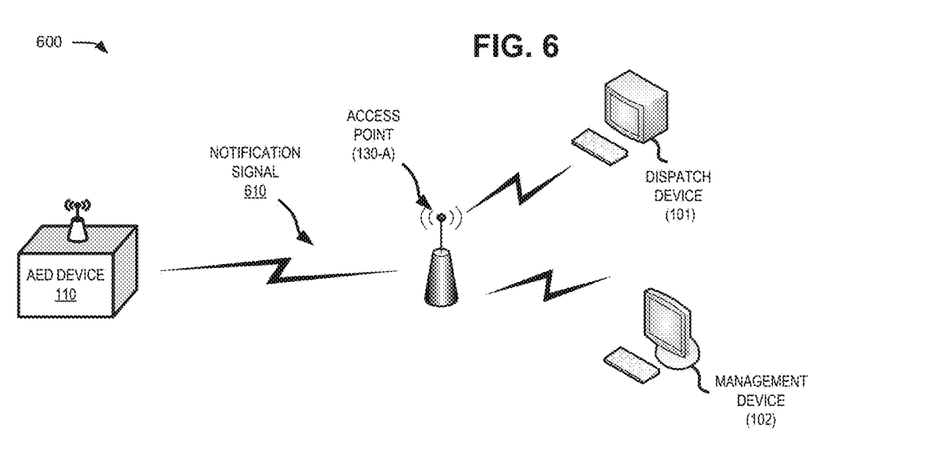

In another example shown in FIG. 6, a portion 600 of environment 100 may include AED device 110, access point 130-A, and dispatch device 101 and/or management device 102. In this example, AED device 110 may forward a notification signal 610 via access point 130-A to dispatch device 101 and/or management device 102 when AED device 110 is activated; when defibrillation is applied through AED device 110 to the patient; and/or when AED device 110 detects an emergency condition. Notification signal 610 may direct dispatch device 101 to send emergency medical assistance to the patient. Notification signal 610 may further include information about the patient that is collected by AED device 110. Notification signal 610 may further direct maintenance device 102 to schedule maintenance on AED device 110 after its use.

Figure 7A:
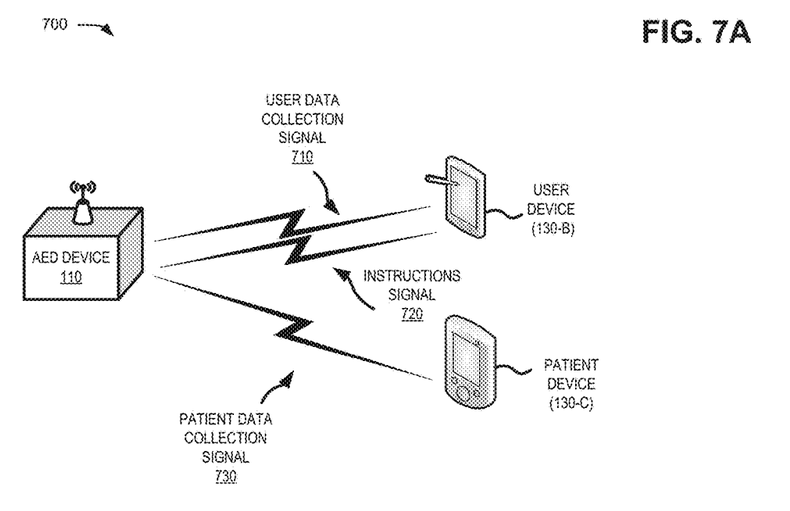
Figure 7B:
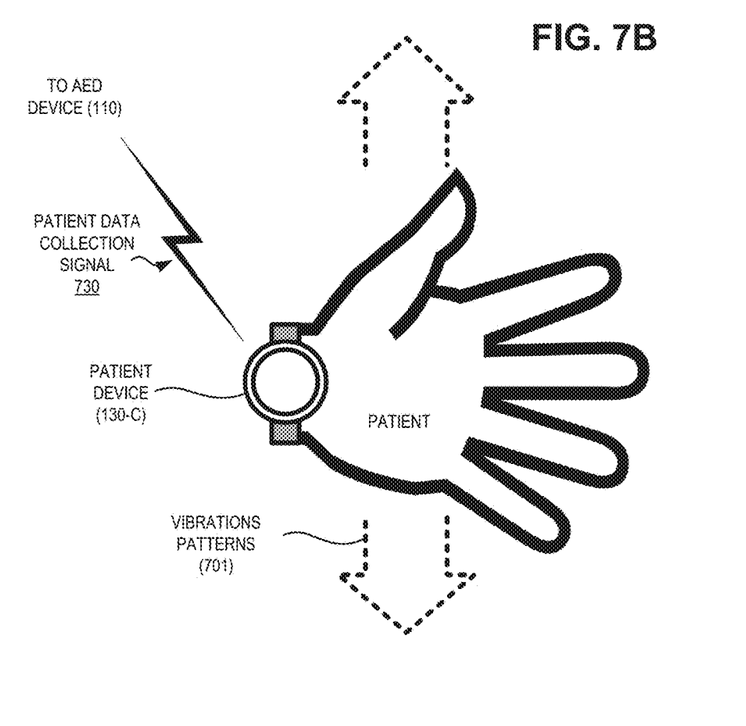

In an example shown in FIGS. 7A and 7B, a portion 700 of environment 100 may include AED device 110, user device 130-B, and/or patient device 130-C. In this example, AED device 110 may exchange user data collection signal 710 with user device 130-B to obtain data stored and/or collected by user device 130-B, such as contact data regarding the user that may be forwarded to dispatch device 101. AED device 110 may further forward an instruction signal 720 to user device 130-B. Instruction signal 720 may include, for example, prompts that may guide the user in using AED device 110. Additionally or alternatively, AED device 110 may exchange patient data collection signal 730 with patient device 130-C to obtain data stored or collected by patient device 130-C, such as accelerometer data collected by patient device 130-C prior to activation of AED device 110.

For example, as shown in FIG. 7B, patient device 130-C may correspond to a wearable device, such as a smart watch, fitness tracker, wearable computer, smart glasses, etc. Patient device 130-C may detect vibrations patterns 701 associated with the patient and may send, in patient data collection signal 730, information identifying the detected vibrations patterns 701. AED device 110 may compare the vibrations pattern 701 with patterns associated with various heart conditions (or other maladies), and AED device 110 may identify a heart condition that matches the detected vibrations pattern 701. For example, vibration patterns 701 may indicate a pattern associated with the patient's heartbeat, and AED device 110 may detect a heart attack when the vibration patterns 701 indicates a particular pattern.

Various preferred embodiments have been described herein with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

It will be apparent that different aspects of the description provided above may be implemented in many different forms of software, firmware, and hardware in the implementations illustrated in the figures. The actual software code or specialized control hardware used to implement these aspects is not limiting of the implementations. Thus, the operation and behavior of these aspects were described without reference to the specific software code—it being understood that software and control hardware can be designed to implement these aspects based on the description herein.

For example, while a series of blocks has been described with respect to FIG. 4, the order of the blocks in process 400 may be modified in other implementations. Furthermore, non-dependent blocks may be performed in parallel. Furthermore, process 400 may include additional and/or fewer blocks than shown in FIG. 4.

In another example, AED device 110 may be configured to be resistant to environmental conditions (e.g., resistant to cold/heat fluctuations, water, dust, static electricity, etc.) so that AED device 110 may continue to operate effectively in various weather and hazardous conditions (e.g., such as in rainy/stormy weather, at locations where moisture/dust is present such as a pool or construction site, during hot/cold days, etc.) without requiring the patient to be moved. Thus, wireless interface module 310 within AED device 110 may also include a level of protection for moisture, weather, dust, static electricity, temperature fluctuations, etc. so that wireless interface module 310 would remain operational in a variety of conditions. For example, wireless interface module 310 may be included in a shielded, insulated, or otherwise protective chassis that encloses other components of AED device 110. In another example, wireless interface module 310 may be surrounded by a first protective enclosure while other components of AED device 110 (e.g., user interface module 320, sensor module 330, and/or defibrillation module 340) are included in a separate protective enclosure. In this example, wireless interface module 310 may further shielded from electrical discharges/interference caused by defibrillation module 340 (e.g., when defibrillation is applied to the patient) or other components of AED device 110 so that communications from wireless interface module 310 are not disrupted. In another example, wireless interface module 310 may schedule transmission during periods when defibrillation is not being applied to the patient and/or AED device 110 is not otherwise performing actions that may disrupt the wireless communications.

No element, act, or instruction used in the present application should be construed as critical or essential unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
   collecting, by a processor included in an automated external defibrillation (AED) device from a patient device, patient data associated with a patient, wherein the patient device includes a sensor to collect patient data, and wherein the patient device is different from the AED device;
   comparing, by the processor, the patient data to historical data previously collected and stored by the patient device;
   identifying, by the processor and based on the comparison, a heart condition associated with the patient;
   forwarding, by the processor, instructions to a user device associated with a user of the AED device, wherein the instructions provide visual prompts that guide the user to apply defibrillation to the patient to address the heart condition, wherein the user device and the AED device are located at a common location, and wherein the user device is coupled to the AED device via a wireless local area network; and
   forwarding, by the processor, a notification to a dispatch device, wherein the notification identifies a location associated with the AED device and an indication that the defibrillation has been applied to the patient, and wherein the dispatch device provides directions to a person who will provide emergency medical assistance at the location.

2. The method of claim 1, wherein collecting the patient data further includes:
   directing the user to attach a second device to the patient; and
   using the second device to collect the patient data.

3. The method of claim 1, wherein collecting the patient data includes:
   establishing wireless communications with the patient device; and
   receiving the patient data from the patient device via the wireless communications.

4. The method of claim 1, wherein the sensor includes an accelerometer and the patient data includes a vibration pattern detected by the accelerometer, and wherein identifying the heart condition includes:
   comparing the detected vibration pattern to a plurality of stored vibration patterns associated with heart conditions; and
   identifying one of the stored vibration patterns that corresponds to the detected vibration pattern, wherein the identified heart condition is associated with the identified stored vibration pattern.

5. The method of claim 1, wherein the notification includes at least one of a machine-to-machine (M2M) communication between the AED device and the dispatch device or an E911 call to the dispatch device.

6. The method of claim 1, wherein forwarding the instructions includes:
   identifying the user device associated with the user;
   establishing wireless communications with the user device via the wireless local area network; and
   forwarding, via the wireless communications, the instructions.

7. The method of claim 1, further comprising:
   determining a status of the AED device;
   forwarding a status signal to a maintenance device, wherein the status signal identifies the status of the AED device; and
   receiving, from the maintenance device, update data based on the status of the AED device.

8. An automated external defibrillation (AED) device comprising:
   a memory configured to store instructions;
   a wireless interface; and
   a processor configured to execute one or more of the instructions to:
     collect, from a patient device that is different than the AED device, patient data associated with a patient;
     compare the patient data to historical data previously collected and stored by the patient device;
     identify, based on the comparison, a heart condition associated with the patient;
     forward guide instructions to a user device associated with a user of the AED device, wherein the guide instructions provide visual prompts to guide the user to apply defibrillation to the patient to address the heart condition, wherein the user device and the AED device are located at a common location, and wherein the user device is connected to the AED device via a wireless local area network; and
     forward, via the wireless interface, a notification to a dispatch device, wherein the notification identifies the heart condition and a location associated with the AED device, and wherein the dispatch device provides directions to a person who will provide emergency medical assistance at the location.

9. The AED device of claim 8, wherein the processor, when collecting the patient data, is further configured to:
   direct the user to attach a sensor on the patient; and
   use the sensor to collect the patient data.

10. The AED device of claim 8, wherein the processor, when collecting the patient data, is further configured to:
   receive the patient data from the patient device via the wireless interface.

11. The AED device of claim 8, wherein the patient device includes a sensor to collect the patient data, wherein the sensor includes an accelerometer and the patient data includes a vibration pattern detected by the accelerometer, and wherein the processor, when identifying the heart condition, is further configured to:
   compare the detected vibration pattern to a plurality of stored vibration patterns associated with heart conditions; and
   identify one of the stored vibration patterns that corresponds to the detected vibration pattern, wherein the identified heart condition is associated with the identified stored vibration pattern.

12. The AED device of claim 8, wherein the notification includes a machine-to-machine (M2M) communication between the AED device and the dispatch device or an E911 call to the dispatch device.

13. The AED device of claim 8, wherein the processor, when forwarding the guide instructions, is further configured to:
   forward the guide instructions via the wireless interface.

14. The AED device of claim 8, wherein the processor is further configured to:
   determine a status of the AED device;
   forward, via the wireless interface, a status signal to a maintenance device, wherein the status signal identifies the status of the AED device, and wherein the maintenance device identifies update data based on the status of the AED device; and
   receive, via the wireless interface and from the maintenance device, the update data.

15. A non-transitory computer-readable medium to store instructions, wherein the instructions comprise:
   one or more instructions that, when executed by a processor included in an automated external defibrillation (AED) device, cause the processor to:
      collect, from a patient device associated with a patient, patient data associated with the patient, wherein the patient device is different from the AED device;
      compare the patient data to historical data collected by the patient device;
      identify, based on the comparison, a heart condition associated with the patient;
      forward guide instructions to a user device associated with a user, wherein the guide instructions provide visual prompts to guide the user to apply defibrillation to the patient to address the heart condition, wherein the user device and the AED device are located at a common location, and wherein the user device is connected to the AED device via a wireless local area network; and
      forward, via a wireless interface, a notification to a dispatch device, wherein the notification identifies a location associated with the AED device, and wherein the dispatch device provides directions to a person who will provide emergency medical assistance at the location.

16. The non-transitory computer-readable medium of claim 15, wherein the one or more instructions further cause the processor, when collecting the patient data, to:
   direct the user to attach a second sensor on the patient; and
   use the second sensor to collect the patient data.

17. The non-transitory computer-readable medium of claim 15, wherein the one or more instructions further cause the processor, when collecting the patient data, to:
   receive the patient data from the patient device via the wireless interface.

18. The non-transitory computer-readable medium of claim 17, wherein the patient device includes a sensor to collect the patient data, wherein the sensor includes an accelerometer and the patient data includes a vibration pattern detected by the accelerometer, and wherein the one or more instructions further cause the processor, when identifying the heart condition, to:
   compare the detected vibration pattern to a plurality of stored vibration patterns associated with heart conditions; and
   identify one of the stored vibration patterns that corresponds to the detected vibration pattern, wherein the identified heart condition is associated with the identified stored vibration pattern.

19. The non-transitory computer-readable medium of claim 15, wherein the one or more instructions further cause the processor, when forwarding the guide instructions, to:
   forward the guide instructions via the wireless interface.

20. The non-transitory computer-readable medium of claim 15, wherein the one or more instructions further cause the processor to:
   determine a status of the AED device;
   forward, via the wireless interface, a status signal to a maintenance device, wherein the status signal identifies the status of the AED device, and wherein the maintenance device identifies update data based on the status of the AED device; and
   receive, via the wireless interface and from the maintenance device, the update data.

* * * * *